(12) United States Patent
Kobayashi et al.

(10) Patent No.: US 11,179,025 B2
(45) Date of Patent: Nov. 23, 2021

(54) IMAGE PICKUP APPARATUS AND ENDOSCOPE

(71) Applicant: OLYMPUS CORPORATION, Tokyo (JP)

(72) Inventors: Hiroshi Kobayashi, Nagano (JP); Takahiro Shimohata, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 110 days.

(21) Appl. No.: 16/676,642

(22) Filed: Nov. 7, 2019

(65) Prior Publication Data

US 2020/0069151 A1 Mar. 5, 2020

Related U.S. Application Data

(63) Continuation of application No. PCT/JP2017/018648, filed on May 18, 2017.

(51) Int. Cl.
*A61B 1/00* (2006.01)
*A61B 1/05* (2006.01)
*A61B 1/06* (2006.01)

(52) U.S. Cl.
CPC ...... *A61B 1/00096* (2013.01); *A61B 1/00045* (2013.01); *A61B 1/051* (2013.01); *A61B 1/0676* (2013.01)

(58) Field of Classification Search
CPC . A61B 1/00096; A61B 1/00045; A61B 1/051; A61B 1/0676; G02B 23/243; G02B 23/2423; G02B 23/2461

(Continued)

(56) References Cited

U.S. PATENT DOCUMENTS 4,890,159 A 12/1989 Ogiu
2012/0293641 A1* 11/2012 Nagamizu .......... A61B 1/00096
348/65

(Continued)

FOREIGN PATENT DOCUMENTS

JP S63-118120 A 5/1988
JP H01-201229 A 8/1989

(Continued)

OTHER PUBLICATIONS

International Search Report dated Jul. 25, 2017 issued in PCT/JP2017/018648.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An image pickup apparatus includes: an optical unit including an incident surface and an emission surface, in which a plurality of optical members are arranged around an optical axis; a polygonal prism image pickup unit including a light receiving surface, a rear surface and a plurality of side faces, in which a plurality of elements including an image pickup device configured to photoelectrically convert light made incident from the optical unit and output an image pickup signal are laminated; and at least one guide, a front portion of which is fixed to the emission surface of the optical unit and a rear portion of which is provided with a plurality of contact surfaces that are respectively in contact with and fixed to the plurality of side faces of the image pickup unit.

18 Claims, 7 Drawing Sheets

(58) Field of Classification Search
USPC .......... 348/65; 362/574; 600/109, 129, 130, 600/175, 176
See application file for complete search history.

(56) References Cited

U.S. PATENT DOCUMENTS

| | | | | |
|---|---|---|---|---|
| 2013/0120647 | A1* | 5/2013 | Negishi | A61B 1/04 348/374 |
| 2016/0178884 | A1* | 6/2016 | Hanada | G02B 27/0025 359/738 |
| 2017/0064162 | A1* | 3/2017 | Haraguchi | A61B 1/00096 |
| 2019/0239734 | A1* | 8/2019 | Yashiro | A61B 1/04 |

FOREIGN PATENT DOCUMENTS

| | | |
|---|---|---|
| JP | H02-058404 U | 4/1990 |
| JP | 5897235 B1 | 3/2016 |
| WO | WO 2015178134 * | 11/2015 |
| WO | WO 2017/073440 A1 | 5/2017 |

* cited by examiner

IMAGE PICKUP APPARATUS AND ENDOSCOPE

CROSS REFERENCE TO RELATED APPLICATION

This application is a continuation application of PCT/JP2017/018648 filed on May 18, 2017, the entire contents of which are incorporated herein by this reference.

BACKGROUND OF THE INVENTION

1. Field of the Invention

The present invention relates to an image pickup apparatus including an optical unit and an image pickup unit, and an endoscope having the image pickup apparatus including the optical unit and the image pickup unit.

2. Description of the Related Art

In recent years, an ultra-small image pickup unit in which a plurality of semiconductor elements including an image pickup device are laminated and which is configured to process and output an image pickup signal outputted by the image pickup device has been developed. By using the above-described image pickup unit in an endoscope, a diameter of a distal end portion can be narrowed and functionality can be improved.

In order to manufacture many kinds of endoscopes in small quantities, it is examined to attach an optical unit according to a specification of the endoscope to an image pickup unit of a standard specification.

Japanese Patent No. 5897235 discloses an image pickup apparatus in which an optical unit is joined to an image pickup device to which cover glass is joined.

SUMMARY OF THE INVENTION

An image pickup apparatus of an embodiment includes: an optical unit including an incident surface and an emission surface, in which a plurality of optical members are arranged around an optical axis; a polygonal prism image pickup unit including a light receiving surface, a rear surface and a plurality of side faces, in which a plurality of elements including an image pickup device configured to photoelectrically convert light made incident from the optical unit and output an image pickup signal are laminated; and at least one guide, a front portion of which is fixed to the emission surface of the optical unit and a rear portion of which is provided with a contact surface that is in contact with and fixed to at least one side face of the image pickup unit.

An endoscope of another embodiment includes an image pickup apparatus, and the image pickup apparatus includes: an optical unit including an incident surface and an emission surface, in which a plurality of optical members are arranged around an optical axis; a polygonal prism image pickup unit including a light receiving surface, a rear surface and a plurality of side faces, in which a plurality of elements including an image pickup device configured to photoelectrically convert light made incident from the optical unit and output an image pickup signal are laminated; and at least one guide, a front portion of which is fixed to the emission surface of the optical unit and a rear portion of which is provided with a contact surface that is in contact with and fixed to at least one side face of the image pickup unit.

DETAILED DESCRIPTION OF THE PREFERRED EMBODIMENTS

First Embodiment

Figure 1:
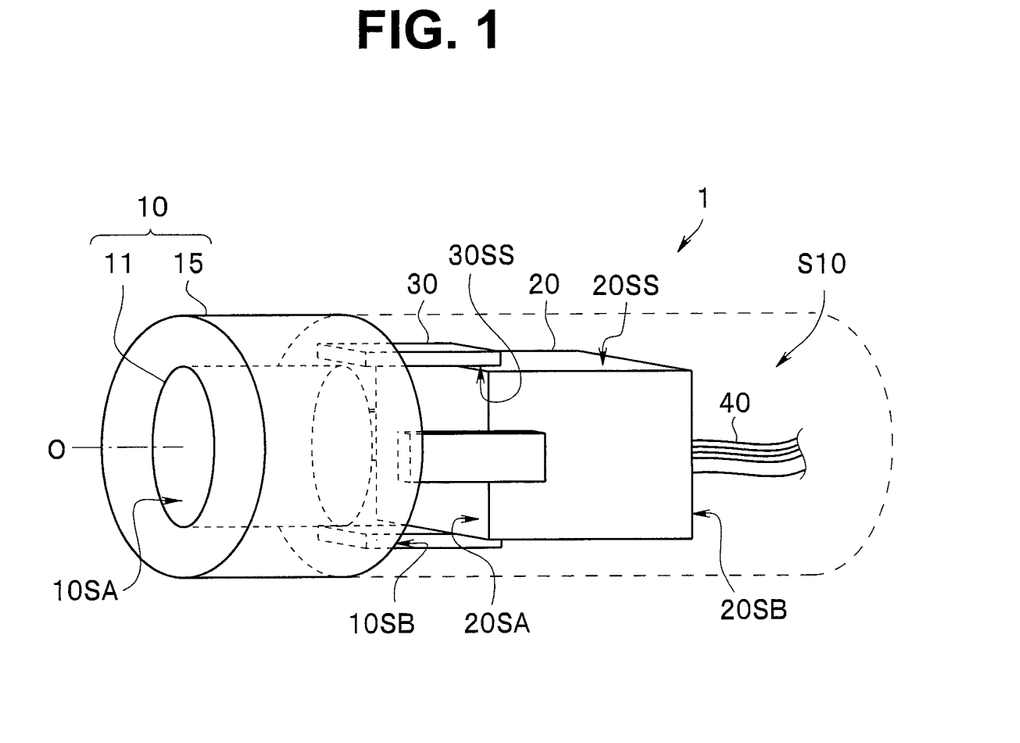
FIG. 1 is a perspective view of an image pickup apparatus of a first embodiment.
Figure 2A:
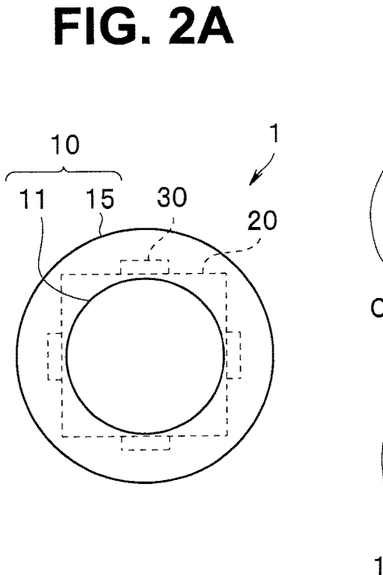
FIG. 2A is a front view of the image pickup apparatus of the first embodiment.
Figure 2B:
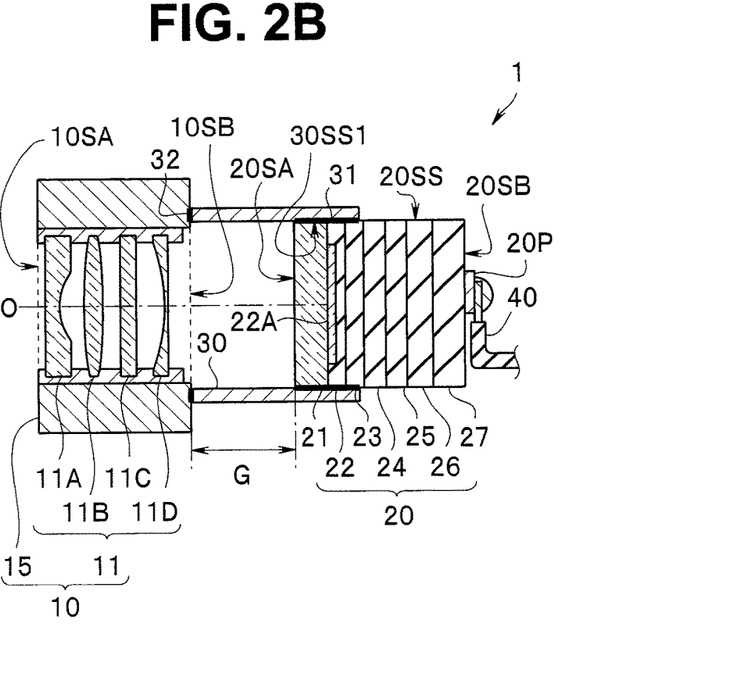
FIG. 2B is a sectional view of the image pickup apparatus of the first embodiment.
Figure 2C:
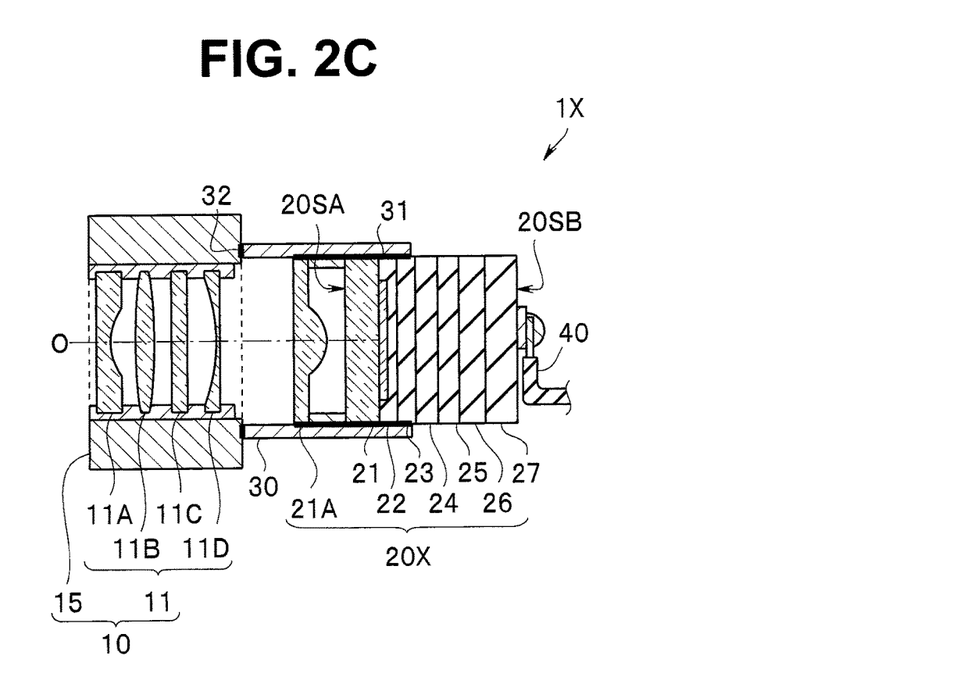
FIG. 2C is a sectional view of the image pickup apparatus of the first embodiment.
Figure 3:
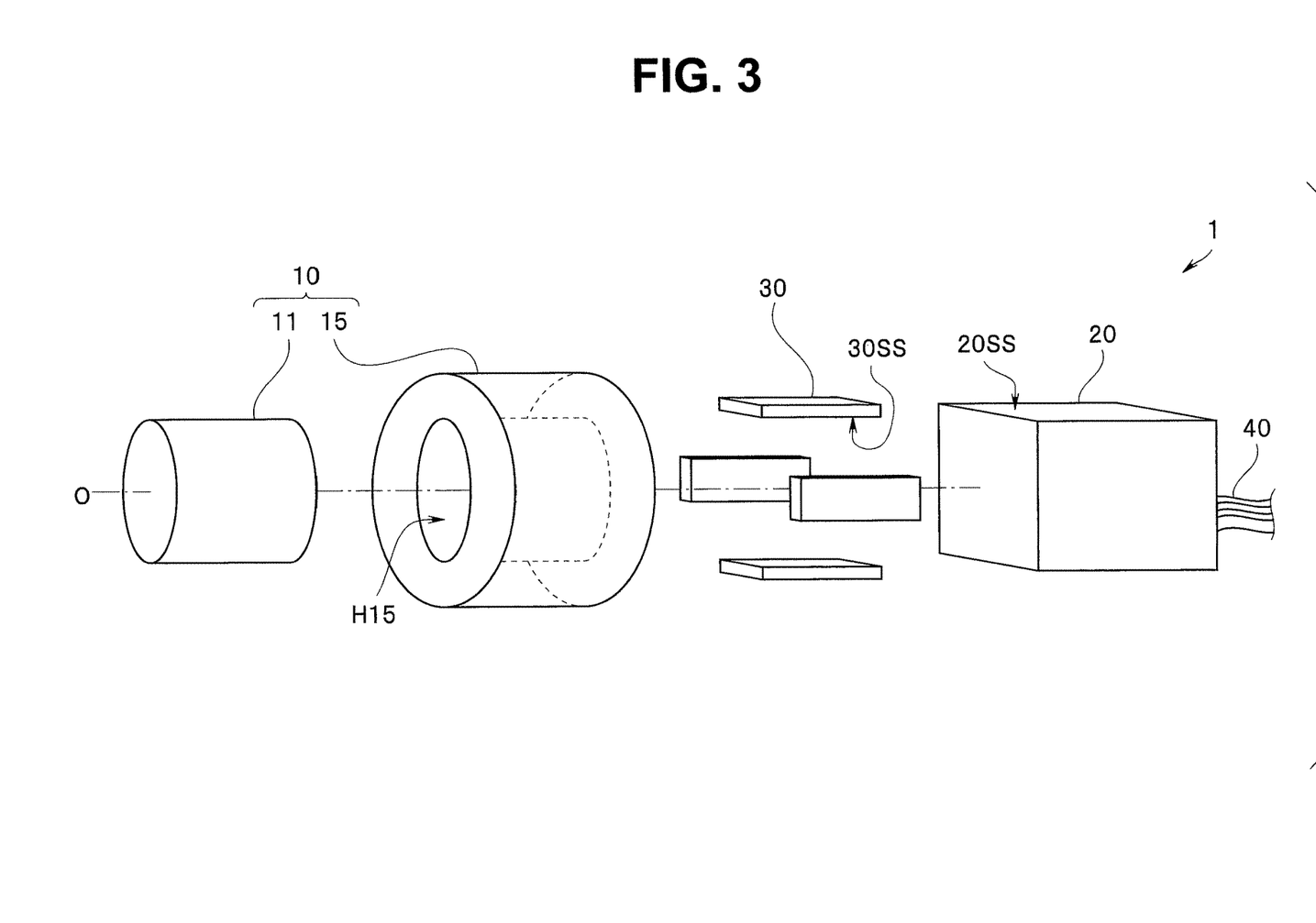
FIG. 3 is an exploded view of the image pickup apparatus of the first embodiment.

An image pickup apparatus 1 of the present embodiment illustrated in FIG. 1 to FIG. 3 includes an optical unit 10, an image pickup unit 20 and a guide 30.

Note that in the following description, the drawings based on the individual embodiments are schematic. A relation between a thickness and a width of individual parts, a ratio of the thicknesses of the respective parts and a relative angle or the like are different from actual ones. Even between the drawings, a part where the relation of mutual dimensions or the ratio is different is sometimes included.

Illustrations of some components are sometimes omitted.

For the image pickup apparatus 1, inside a space S10 where the optical unit 10 is extended in a direction of an optical axis (O), the image pickup unit 20, the guide 30 and a distal end portion of a signal cable 40 are disposed. An outer diameter of the image pickup apparatus 1 designed especially for an endoscope is the same as an outer diameter of the optical unit 10, and is as narrow as 5 mm or less, for example. Note that a length in an optical axis direction is also 10 mm or less, for example, and the image pickup apparatus 1 is ultra-small.

The optical unit 10 including an incident surface 10SA and an emission surface 10SB on an opposite side of the incident surface 10SA includes a frame member 15 and an optical member 11. For the optical member 11, a plurality of optical members 11A-11D are arranged at a lens frame around the optical axis (O). The optical members 11A, 11B and 11D are lenses and the optical member 11C is a parallel planar filter formed of an infrared ray cutting material that eliminates infrared rays. The optical member 11 is inserted into a through-hole H15 of the frame member (optical holder) 15. As described later, in the optical unit 10, the frame member 15 and the lens frame of the optical member 11 may be an integrated member.

The image pickup unit 20 is a quadrangular prism including a light receiving surface 20SA, a rear surface 20SB on the opposite side of the light receiving surface 20SA and four side faces 20SS. In the image pickup unit 20, a plurality of planar semiconductor elements (semiconductor chips) 22-27 including a planar image pickup device (image pickup chip) 22 to which cover glass 21 is joined are laminated. The image pickup device 22 photoelectrically converts incident light from the optical unit 10 and outputs an image pickup signal.

Note that on a front surface of the image pickup device 22 of the image pickup unit 20, not only the cover glass 21 but also a plurality of optical members such as lenses may be disposed. For example, in an image pickup unit 20X of an image pickup apparatus 1X illustrated in FIG. 2C, an optical member 21A of a convex lens or the like is disposed on the front surface of the cover glass 21. In other words, the optical unit 10 may be an extension lens unit of the image pickup unit 20 where the plurality of optical members are disposed.

The image pickup device 22 includes a light receiving portion 22A formed of a CCD or CMOS image pickup portion. The image pickup device 22 may be either an FSI type image sensor or a BSI type image sensor.

The semiconductor elements 23-27 primarily process the image pickup signal outputted by the image pickup device 22 and process a control signal that controls the image pickup device 22. For example, the semiconductor elements 23-27 include an AD conversion circuit, a memory, a transmission and output circuit, a filter circuit, a thin film capacitor, and a thin film inductor. The number of the semiconductor elements 22-27 included in the image pickup unit 20 is three or larger and ten or smaller, for example. The plurality of semiconductor elements 22-27 are electrically connected to one another via through wiring (not illustrated) respectively, and a plurality of connection electrodes 20P are disposed on a rear surface of the semiconductor element 27 arranged rearmost, that is, on the rear surface 20SB of the image pickup unit 20.

The image pickup unit 20 is manufactured by cutting processing of a laminated wafer in which a cover glass wafer, an image pickup wafer including the plurality of image pickup devices 22 and a plurality of element wafers each including the plurality of semiconductor elements 23-27 are laminated. Thus, the image pickup unit 20 is a rectangular parallelepiped (quadrangular prism) the four side faces 20SS of which are cut sections of a relatively large area. The side faces 20SS may be coated with a light shielding resin.

The plurality of signal cables 40 configured to supply power to the image pickup unit 20 and transmit the image pickup signal are bonded with each of the plurality of connection electrodes 20P. Note that the signal cables 40 may be connected with the image pickup unit 20 in a state of interposing a relay member such as an MID solid wiring board, an Si interposer, a TAB tape with a flying lead, a ceramic wiring board or a glass wiring board bonded with the connection electrodes 20P of the image pickup unit 20. In this case, the relay member is also housed inside the space S10.

A front portion of the guide 30 which is the side plate is fixed to an outer peripheral portion of the emission surface 10SB of the optical unit 10. The guide 30 is joined to the emission surface 10SB by a first adhesive material 32. The front portion of the guide 30 may be inserted into a hole of the emission surface 10SB and joined. Further, as described later, the guide 30 may be a member integrated with the optical unit 10, that is, a part of the optical unit 10.

A rear portion of the guide 30 is provided with four contact surfaces 30SS1 that are respectively in contact with and fixed to the four side faces 20SS of the image pickup unit 20. The contact surfaces 30SS1 of the guide 30 are fixed to the side faces 20SS of the image pickup unit 20 by a second adhesive material 31. In other words, since the image pickup unit 20 is a laminated element in which the cover glass 21 and the plurality of elements 22-27 are laminated, a length in an optical axis direction is long compared to the image pickup device 22 in which the other semiconductor elements 23-27 are not laminated. Since the area of the side faces 20SS of the image pickup unit 20 is large in the image pickup apparatus 1, the contact surfaces 30SS1 of the guide 30 can be stably fixed.

In the image pickup apparatus 1, each of contact surfaces 30SS of the four guides 30 is in contact with each of the four side faces 20SS of the rectangular parallelepiped image pickup unit 20. Thus, a relative position in an optical axis orthogonal direction (in-plane direction) of the optical unit 10 and the image pickup unit 20 is defined by the guides 30. In other words, the optical axis of the optical unit 10 and the optical axis of the image pickup unit 20 are automatically positioned by the four guides 30.

Even though the image pickup apparatus 1 is ultra-small, the optical unit 10 and the image pickup unit 20 can be accurately and stably fixed so that productivity is high. Note that it is sufficient when the contact surfaces 30SS of the at least two orthogonally arranged guides 30 are in contact with the two side faces 20SS of the image pickup unit 20. Note that even when only one guide 30 is provided, one direction of the two in-plane directions is defined. In other words, while the image pickup apparatus 1 includes the plurality of guides 30, it is sufficient when the image pickup apparatus of the present invention includes at least one guide 30.

It is not necessary for all of the plurality of guides 30 to have the same shape.

In the image pickup apparatus 1, between the emission surface 10SB of the optical unit 10 and the light receiving surface 20SA of the image pickup unit 20, there is a gap (space) of a length G. In the image pickup apparatus 1, a distance between the optical unit 10 and the image pickup unit 20, that is, an optical path length, is adjustable for each apparatus.

Modifications of First Embodiment

Since image pickup apparatuses 1A-1F of the modifications of the first embodiment are similar to the image pickup apparatus 1 and have the same effects, the same signs are attached to the components of the same functions and the description is omitted.

Modification 1 of First Embodiment

Figure 4:
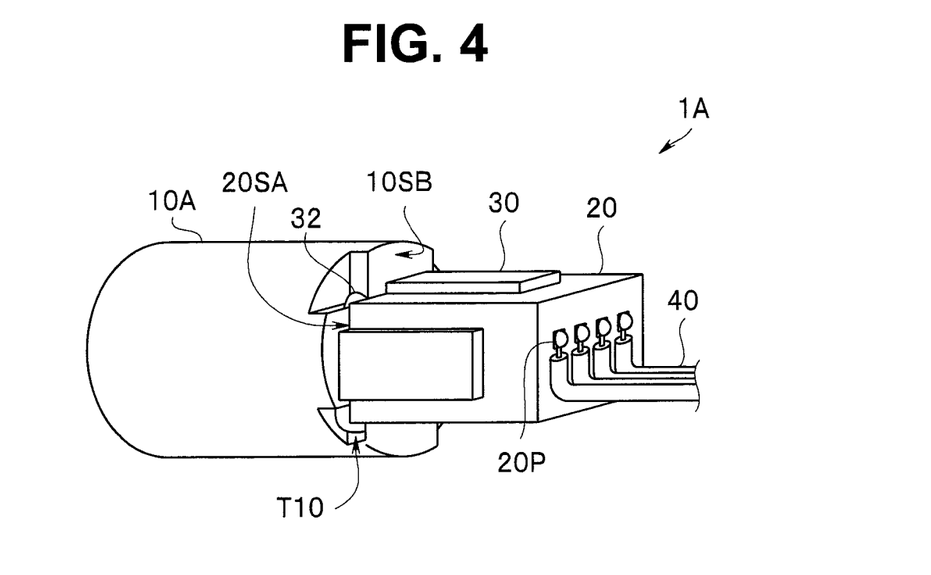
FIG. 4 is a perspective view of the image pickup apparatus of a modification 1 of the first embodiment.

In the image pickup apparatus 1A of the present modification illustrated in FIG. 4, the emission surface 10SB of an optical unit 10A is joined with the light receiving surface 20SA of the image pickup unit 20 by the first adhesive material 32. In the image pickup apparatus 1A, the distance between the optical unit 10 and the image pickup unit 20, that is, the optical path length, is uniquely defined.

Here, similarly to the optical unit 10 illustrated in FIG. 2B, on the emission surface 10SB of the optical unit 10A, an optical path area is an opening.

There is a risk that the excess first adhesive material 32 infiltrates the opening of the emission surface 10SB. Then, a part of an optical path is blocked by the first adhesive material 32. However, in the optical unit 10A, a recessed portion T10 is formed at a corner of a peripheral surface of the optical path area of the emission surface 10SB. Thus, when the emission surface 10SB is joined with the light receiving surface 20SA by the first adhesive material 32, the excess first adhesive material 32 is housed in the recessed portion T10. In other words, the first adhesive material 32 is also disposed in the recessed portion T10.

Since there is no risk that the excess first adhesive material 32 infiltrates the opening of the emission surface 10SB in the image pickup apparatus 1A, an optical characteristic is stable.

Modification 2 of First Embodiment

Figure 5A:
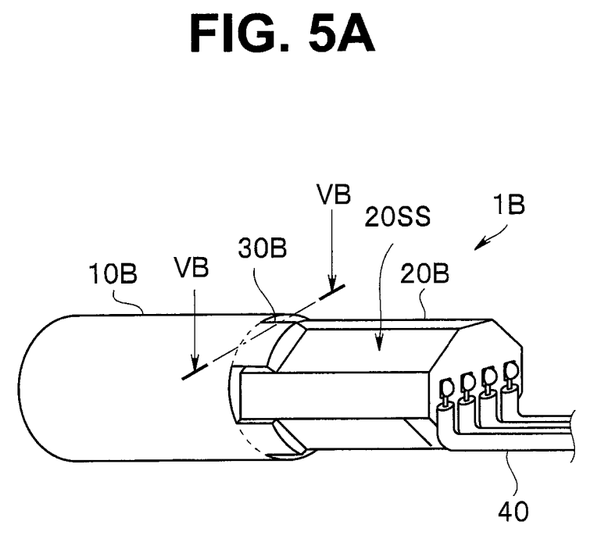
FIG. 5A is a perspective view of the image pickup apparatus of a modification 2 of the first embodiment.
Figure 5B:
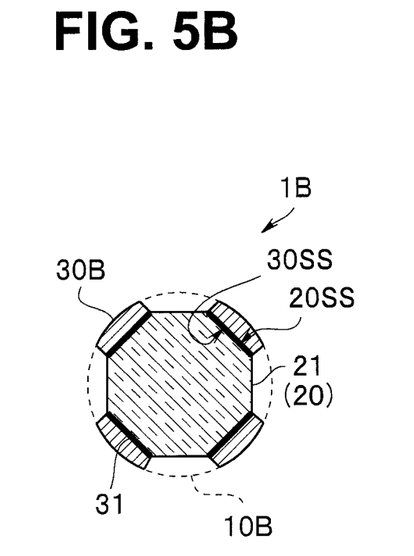
FIG. 5B is a sectional view along a VB-VB line in FIG. 5A of the image pickup apparatus of the modification 2 of the first embodiment.

In an image pickup apparatus 1B of the present modification illustrated in FIG. 5A and FIG. 5B, a guide 30B which is a side plate is a member integrated with an optical unit 10B. In other words, the optical unit 10B includes the four guides 30B protruding backwards from the emission surface 10SB. An outer surface of the guide 30B is a curved surface continuing with an outer surface of the optical unit 10B. An inner surface of the guide 30B is the contact surface 30SS in contact with the side face 20SS of an image pickup unit 20B.

The image pickup unit 20B is a hexagonal prism for which corner portions in an optical axis parallel direction of a rectangular parallelepiped are chamfered. Four surfaces of the six side faces 20SS of the image pickup unit 20B are joined with the contact surfaces of the guides 30B respectively.

Even when the image pickup unit 20B includes the light receiving portion 22A of the area larger than the area of the light receiving portion 22A in the image pickup unit 20 or the like, for example, since the corner portions are chamfered, the image pickup unit 20B is housed inside the space S10. Thus, the image pickup apparatus 1B can achieve high image quality without increasing the outer diameter.

In other words, the image pickup unit 20 of the image pickup apparatuses 1 and 1A is the rectangular parallelepiped (quadrangular prism). However, the image pickup unit of the present invention may be the hexagonal prism with the chamfered corner portions like the image pickup apparatus 1B or may be a practically polygonal prism for which the corner portions of the polygonal prism are curved or the like, as long as the image pickup unit is a polygonal prism (polygonal pillar shape) including four or more side faces. Note that though not illustrated, the optical unit may also be a polygonal prism or a practically polygonal prism for which the corner portions are curved.

Modification 3 of First Embodiment

Figure 6:
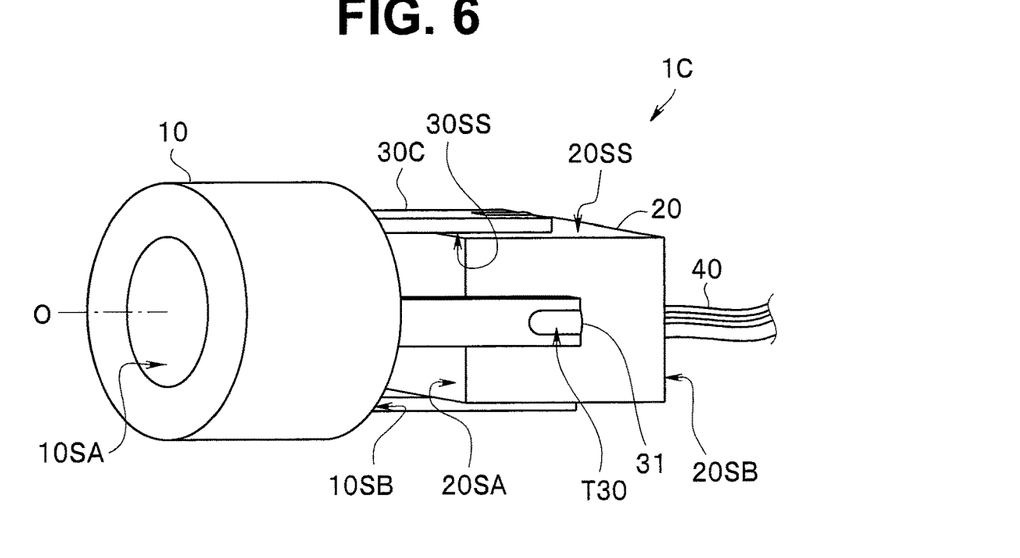
FIG. 6 is a perspective view of the image pickup apparatus of a modification 3 of the first embodiment.

In an image pickup apparatus 1C of the present modification illustrated in FIG. 6, the contact surface 30SS of a guide 30C which is the side plate is provided with a groove (notch) T30 opened at a rear end. The second adhesive material 31 is also disposed in the groove T30.

In the image pickup apparatus 1C, for the guide 30C, not only the contact surface 30SS but also the inner surface of the groove T30 is fixed with the side face 20SS of the image pickup unit 20 by the second adhesive material 31. Thus, the optical unit 10 and the image pickup unit 20 are strongly fixed.

Note that even when the guide 30 is provided with a hole instead of the groove or is provided with the groove and the hole, it goes without saying that the same effect as the image pickup apparatus 1C is provided. At least one of the plurality of guides 30 may be provided with the groove or the like.

Modification 4 of First Embodiment

Figure 7A:
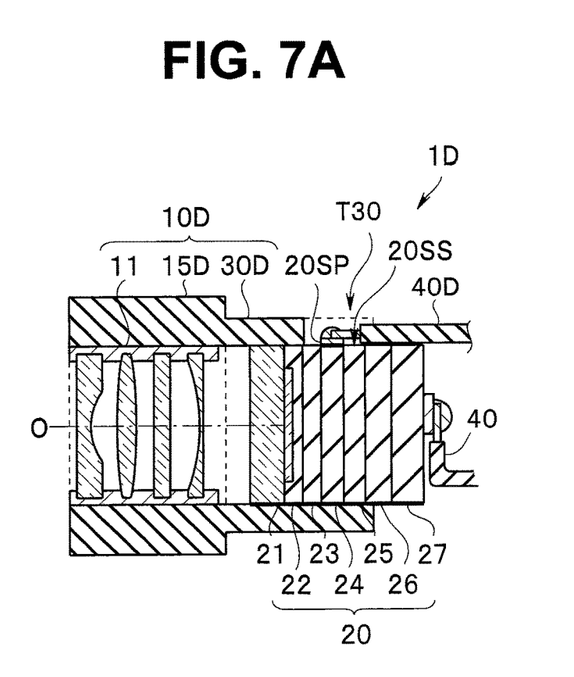
FIG. 7A is a sectional view of the image pickup apparatus of a modification 4 of the first embodiment.
Figure 7B:
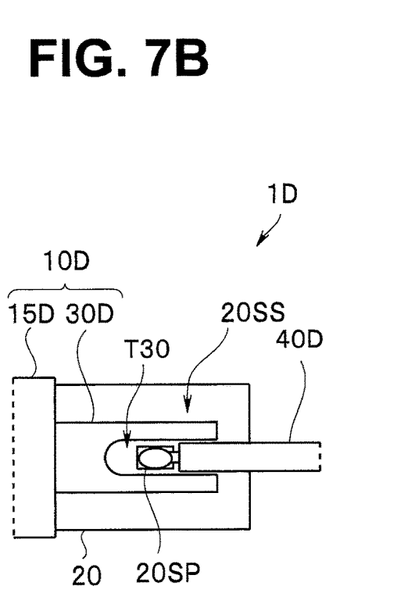
FIG. 7B is a top view of the image pickup apparatus of the modification 4 of the first embodiment.

In an image pickup apparatus 1D of the present modification illustrated in FIG. 7A and FIG. 7B, similarly to the image pickup apparatus 1C, a guide 30D which is the side plate is provided with the groove T30. While the guide and the optical unit are separate members in the image pickup apparatuses 1 and 1A-1C, the guide 30D is the member integrated with an optical unit 10D.

In an image pickup unit 20D, a side face electrode 20SP is disposed on the side face 20SS. The side face electrode 20SP is, for example, a common ground potential electrode of the plurality of semiconductor elements 22-27. Then, the guide 30D is disposed to the image pickup unit 20D in the state of arranging the side face electrode 20SP in the opening of the groove T30. A ground potential cable 40D which is one of the plurality of signal cables 40 is inserted into the groove T30 and bonded with the side face electrode 20SP.

Note that it is sufficient when the side face electrode 20SP is disposed to at least one side face 20SS of the plurality of side faces 20SS and at least one guide 30D of the plurality of guides 30 is provided with the groove T30.

For the image pickup unit 20D, it is easy to position the ground potential cable 40D at a position of the side face electrode 20SP of the image pickup unit 20D. In other words, a width of the groove T30 is set to be almost the same as (to be slightly larger than, strictly) a coat of the ground potential cable 40D.

Note that in the image pickup apparatus 1D, a distal end portion of the ground potential cable 40D is also arranged inside the space S10 where the optical unit 10 is extended in the direction of the optical axis (0).

Modification 5 of First Embodiment

Figure 8A:
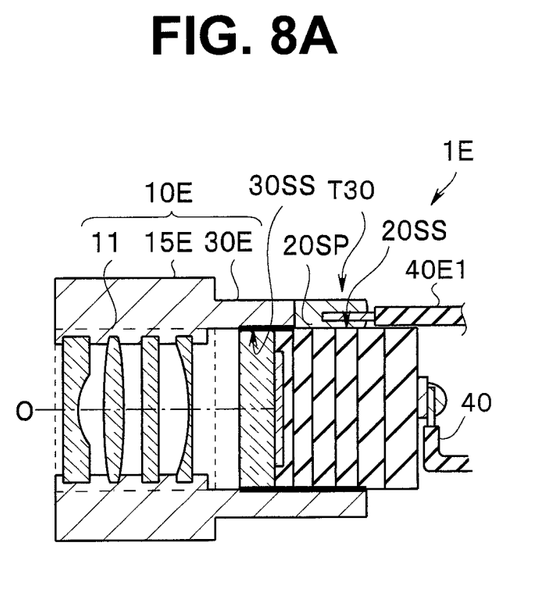
FIG. 8A is a sectional view of the image pickup apparatus of a modification 5 of the first embodiment.
Figure 8B:
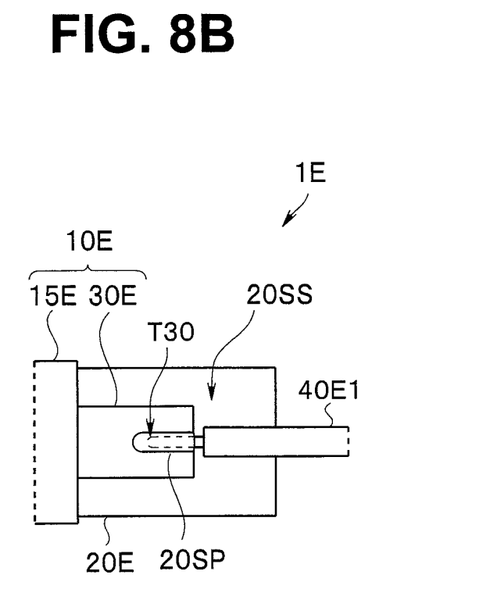
FIG. 8B is a top view of the image pickup apparatus of the modification 5 of the first embodiment.

In an image pickup apparatus 1E of the present modification illustrated in FIG. 8A and FIG. 8B, the contact surface 30SS of a guide 30E which is the side plate is provided with the groove (notch) T30 opened at the rear end. The frame member 15 including the guide 30E of an optical unit 10E is formed of a conductor integrated with the lens frame of the optical member 11 as well, for example, stainless steel, a surface of which is copper-plated.

A signal cable 40E1 which is a ground potential line inserted into the groove T30 is solder-bonded with the side face electrode 20SP and the frame member 15. The width of the groove T30 is set to be almost the same as (to be slightly larger than, strictly) a core wire of the ground potential cable 40D.

In the image pickup apparatus 1E, since a frame member 15E is a ground potential, there is no risk of adversely affecting the image pickup device 22 or the like by electrification. Note that the outer surface of the frame member 15 may be covered with an insulating resin.

Note that in the image pickup apparatus 1E, the guide 30E may be solder-bonded with the image pickup unit 20 without interposing the second adhesive material 31.

Modification 6 of First Embodiment

Figure 9A:
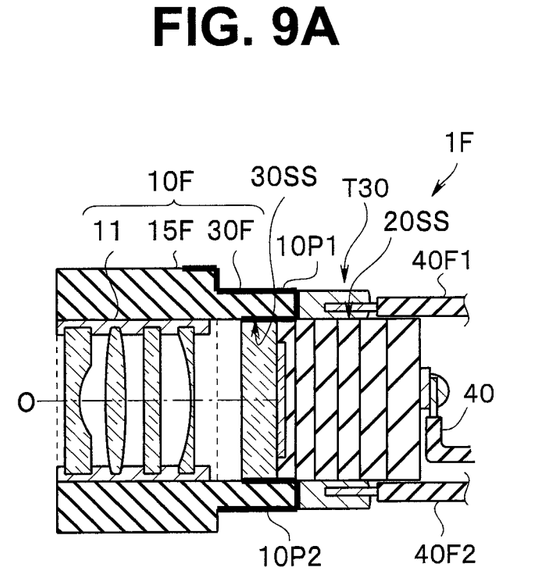
FIG. 9A is a sectional view of the image pickup apparatus of a modification 6 of the first embodiment.
Figure 9B:
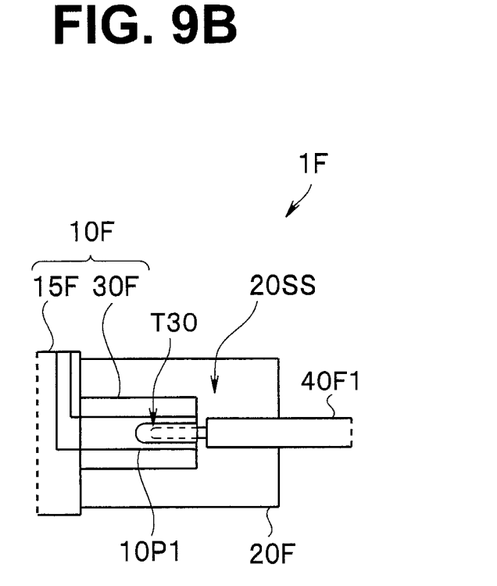
FIG. 9B is a top view of the image pickup apparatus of the modification 6 of the first embodiment.

In an image pickup apparatus 1F of the present modification illustrated in FIG. 9A and FIG. 9B, the contact surface 30SS of a guide 30F which is the side plate is provided with the groove (notch) T30 opened at the rear end. The frame member 15 including the guide 30F of an optical unit 10F is formed of the MID solid wiring board including front wiring, for example.

Signal cables 40F1 and 40F2 are bonded with respective wiring formed of the conductor of the guide 30F. The signal cable 40F1 which is the ground potential line is bonded with the side face electrode (not illustrated) of an image pickup unit 20F by going through wiring 10P1 of the guide 30F. The signal cable 40F2 which is a power line is bonded with the different side face electrode (not illustrated) of the image pickup unit 20F by going through different wiring 10P2 of the guide 30F.

In the image pickup apparatus 1F, there is no risk that the image pickup signal or the like is adversely affected by a power signal since the signal cable 40F2 which is the power line is bonded at a position separated from the signal cable 40 that transmits the image pickup signal or the like.

Note that in the image pickup apparatus 1F, the distal end portions of the signal cable 40F1 which is the ground potential line and the signal cable 40F2 which is the power line are also arranged inside the space S10 where the optical unit 10 is extended in the direction of the optical axis (O).

Second Embodiment

Figure 10:
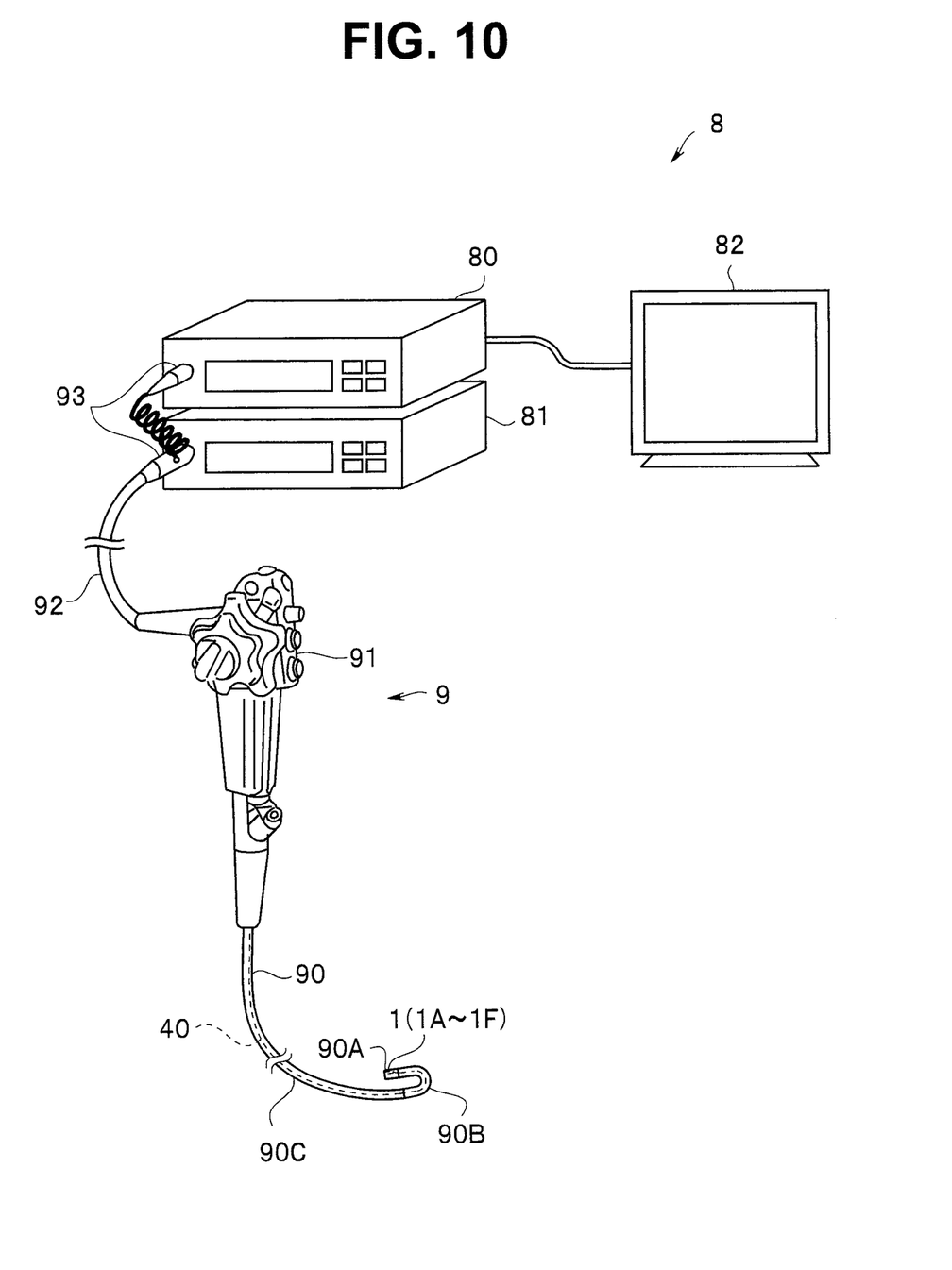
FIG. 10 is a perspective view of an endoscope system including an endoscope of a second embodiment.

An endoscope system 8 including an endoscope 9 of the present embodiment illustrated in FIG. 10 includes the endoscope 9, a processor 80, a light source device 81, and a monitor 82. The endoscope 9 includes an insertion portion 90, an operation portion 91 and a universal cord 92. The insertion portion 90 is inserted into a body cavity of a subject, and the endoscope 9 photographs an in-vivo image of the subject and outputs an image signal.

The insertion portion 90 is configured by a distal end portion 90A where the image pickup apparatus 1 or 1A-1F (hereinafter, referred to as the image pickup apparatus 1 or the like) is disposed, a freely bendable bending portion 90B connected to a proximal end side of the distal end portion 90A, and a flexible portion 90C connected to the proximal end side of the bending portion 90B. The bending portion 90B is bent by an operation of the operation portion 91. Note that the endoscope 9 may be a rigid endoscope or may be a capsule type endoscope.

On the proximal end side of the insertion portion 90 of the endoscope 9, the operation portion 91 provided with various kinds of buttons that operate the endoscope 9 is disposed.

The light source device 81 includes a white LED, for example. Illumination light emitted by the light source device 81 is guided to the distal end portion 90A by going through a light guide (not illustrated) inserted through the universal cord 92 and the insertion portion 90, and illuminates the subject.

The endoscope 9 includes the insertion portion 90, the operation portion 91 and the universal cord 92, and transmits the image pickup signal outputted by the image pickup apparatus 1 or the like disposed in the distal end portion 90A of the insertion portion 90 through the signal cable 40 inserted through the insertion portion 90.

Since the image pickup apparatus 1 is ultra-small and highly productive, the endoscope 9 including the image pickup apparatus 1 is lowly invasive because the diameter of the distal end portion 90A of the insertion portion 90 is narrow, and is highly productive. In addition, the endoscopes including the image pickup apparatuses 1A-1F have the effects of the respective image pickup apparatuses.

The present invention is not limited to the embodiments and the modifications or the like described above, but can be variously changed, combined and applied without changing a subject matter of the present invention.

What is claimed is:

1. An image pickup apparatus comprising:
   an optical frame including a distal surface upon which light is incident and a proximal end face, the optical frame housing a plurality of optics arranged around an optical axis;
   an image pickup unit having a polygonal prism shape including a light receiving distal end face, a proximal surface and a plurality of side faces offset from the distal end face and from the proximal surface, the image pickup unit including a plurality of laminated elements including an image pickup sensor configured to photoelectrically convert light from the optical frame and to output an image pickup signal; and
   at least one guide, a distal portion of the at least one guide being fixed to the proximal end face of the optical frame and a proximal portion of the at least one guide being provided with a contact surface that is in contact with and fixed to at least one of the plurality of side faces of the image pickup unit.

2. The image pickup apparatus according to claim 1, wherein the at least one guide comprises a plurality of guides, wherein the plurality of guides are in contact with a corresponding one of the plurality of side faces of the image pickup unit.

3. The image pickup apparatus according to claim 1, wherein the guide and the optical frame are separate members.

4. The image pickup apparatus according to claim 1, wherein a gap is provided between the proximal end face of the optical frame and the distal end face of the image pickup unit.

5. The image pickup apparatus according to claim 1, wherein
   proximal end face of the optical frame is joined with the distal end face of the image pickup unit by a first adhesive material, and
   a recess is formed on the proximal end face of the optical frame, the recess being configured such that excess first adhesive material flows into the recess.

6. The image pickup apparatus according to claim 1, wherein the guide is provided with a hole or a notch, the contact surface of the guide and the corresponding one of the plurality of side faces of the image pickup unit are joined by a second adhesive material, and the second adhesive material is also disposed in the hole or the notch.

7. The image pickup apparatus according to claim 1, further comprising
   a signal cable electrically connected with the image pickup unit,
   wherein the contact surface of the guide is provided with a groove opened at a rear end, the image pickup unit includes a side face electrode on the side face, the guide is disposed on the image pickup unit in a state where the side face electrode is arranged in the groove, and the signal cable inserted into the groove is bonded with the side face electrode.

8. The image pickup apparatus according to claim 7, wherein the guide includes wiring formed of a conductor, and the signal cable is bonded with the side face electrode and the wiring.

9. The image pickup apparatus according to claim 7, wherein the image pickup unit, the guide and a distal end portion of the signal cable are disposed inside a space where the distal surface of the optical frame is extended in a direction of the optical axis.

10. An endoscope comprising an image pickup apparatus, wherein the image pickup apparatus includes: an optical frame including a distal surface upon which light is incident and a proximal end face, the optical frame housing a plurality of optics arranged around an optical axis; an image pickup unit having a polygonal prism shape including a light receiving distal end face, a proximal surface and a plurality of side faces offset from the distal end face and from the proximal surface, the image pickup unit including a plurality of laminated elements including an image pickup sensor configured to photoelectrically convert light from the optical frame and to output an image pickup signal; and at least one guide, a distal portion of the at least one guide being fixed to the proximal end face of the optical frame and a proximal portion of the at least one guide being provided with a contact surface that is in contact with and fixed to at least one of the plurality of side faces of the image pickup unit.

11. The endoscope according to claim 10, wherein the at least one guide comprises a plurality of guides, wherein the plurality of guides are in contact with a corresponding one of the plurality of side faces of the image pickup unit.

12. The endoscope according to claim 10, wherein the guide and the optical frame are separate members.

13. The endoscope according to claim 10, wherein a gap is provided between the proximal end face of the optical frame and the distal end face of the image pickup unit.

14. The endoscope according to claim 10, wherein the proximal end face of the optical frame is joined with the distal end face of the image pickup unit by a first adhesive material, and a recess is formed on the proximal end face of the optical frame, the recess being configured such that excess first adhesive material flows into the recess.

15. The endoscope according to claim 10, wherein the guide is provided with a hole or a notch, the contact surface of the guide and the corresponding one of the plurality of side faces of the image pickup unit are joined by a second adhesive material, and the second adhesive material is also disposed in the hole or the notch.

16. The endoscope according to claim 10, further comprising a signal cable electrically connected with the image pickup unit, wherein the contact surface of the guide is provided with a groove opened at a rear end, the image pickup unit includes a side face electrode on the side face, the guide is disposed on the image pickup unit in a state where the side face electrode is arranged in the groove, and the signal cable inserted into the groove is bonded with the side face electrode.

17. The endoscope according to claim 16, wherein the guide includes wiring formed of a conductor, and the signal cable is bonded with the side face electrode and the wiring.

18. The endoscope according to claim 16, wherein the image pickup unit, the guide and a distal end portion of the signal cable are disposed inside a space where the distal surface of the optical frame it is extended in a direction of the optical axis.

* * * * *